(12) United States Patent
Geng et al.

(10) Patent No.: US 7,691,803 B1
(45) Date of Patent: Apr. 6, 2010

(54) PROPANOL AND RELATED COMPOUNDS AND THEIR USE IN PERFUME COMPOSITIONS

(75) Inventors: Feng Geng, Piscataway, NJ (US); Richard M. Boden, Ocean, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 12/269,473

(22) Filed: Nov. 12, 2008

(51) Int. Cl.
*A61K 8/18* (2006.01)
*C11D 3/50* (2006.01)
*C07C 35/20* (2006.01)

(52) U.S. Cl. .................. 512/25; 510/104; 568/821
(58) Field of Classification Search ............... 568/376, 568/821; 512/25, 27; 510/104
See application file for complete search history.

(56) References Cited

OTHER PUBLICATIONS

Koval'Skaya et al. HCAPLUS document No. 131:214435, Accession No. 1999:39885, (1998).*
Shiraishi et al. Organic Letters, 2008, vol. 10 (14), p. 3117-3120.*
Chow et al. Journal of the American Chemical Society, 1986, vol. 108 (6), p. 1234-1239.*
Bailey et al. Journal of the American Chemical Society, 1992, vol. 114 (21), p. 8053-8060.*
Koval'skaya et al. Russian Journal of Organic Chemistry (1998), 34(10), 1449-1454. HCAPLUS abstract, Accession No. 1999:398885; Document No. 131:214435.*

* cited by examiner

*Primary Examiner*—Sikarl A Witherspoon
(74) *Attorney, Agent, or Firm*—Elizabeth M. Quirk; XuFan Tseng; Joseph F. Leightner

(57) ABSTRACT

The present invention a method of improving, enhancing or modifying a fragrance formulation through the addition of an olfactory acceptable amount of a compound of formula:

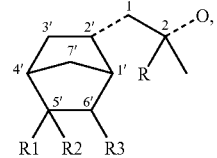

wherein R is absent, hydrogen or methyl;
R1, R2, and R3 are independently hydrogen or methyl; and
the broken lines represent independently single or double bonds, with the proviso that when R1, R2, and R3 are hydrogen, R is methyl.

12 Claims, No Drawings

PROPANOL AND RELATED COMPOUNDS AND THEIR USE IN PERFUME COMPOSITIONS

FIELD OF THE INVENTION

The present invention relates to new chemical entities and the incorporation and use of the new chemical entities as fragrance materials.

BACKGROUND OF THE INVENTION

There is an ongoing need in the fragrance industry to provide new chemicals to give perfumers and other persons the ability to create new fragrances for perfumes, colognes and personal care products. Those with skill in the art appreciate how differences in the chemical structure of the molecule can result in significant differences in the odor, notes and characteristics of a molecule. These variations and the ongoing need to discover and use the new chemicals in the development of new fragrances allow the perfumers to apply the new compounds in creating new fragrances.

SUMMARY OF THE INVENTION

The present invention provides novel chemicals, and the use of the chemicals to enhance the fragrance of perfumes, toilet waters, colognes, personal products and the like. In addition, the present invention is directed to the use of the novel chemicals to enhance fragrance in perfumes, toilet waters, colognes, personal products and the like.

More specifically, the present invention is directed to novel propanol and related compounds and a method of improving, enhancing or modifying a fragrance formulation through the addition of an olfactory acceptable amount of the novel propanol and related compounds represented by Formula I set forth below:

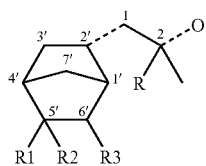

Formula I wherein R is absent, hydrogen or methyl;
R1, R2, and R3 are independently hydrogen or methyl; and
the broken lines represent independently single or double bonds, with the proviso that when R1, R2, and R3 are hydrogen, R is methyl.

Another embodiment of the invention is directed to a fragrance formulation comprising the propanol and related compounds provided above.

Another embodiment of the invention is directed to a method for enhancing a perfume composition by incorporating an olfactory acceptable amount of the propanol and related compounds provided above.

These and other embodiments of the present invention will be apparent by reading the following specification.

DETAILED DESCRIPTION OF THE INVENTION

In Formulae I above, R is absent, hydrogen or methyl; R1, R2, and R3 are independently hydrogen or methyl; and the broken lines at the 2 and 2' positions represent independently single and/or double bonds, with the proviso that when R1, R2, and R3 are all hydrogen, R is methyl.

In one embodiment of the invention, the novel compounds of the invention are represented by the following structures:

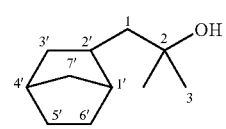

Formula II

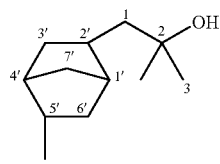

Formula III

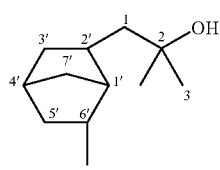

Formula IV

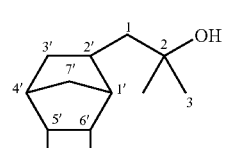

Formula V

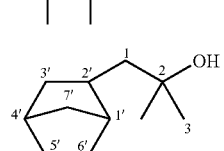

Formula VI

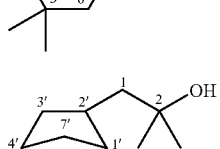

Formula VII

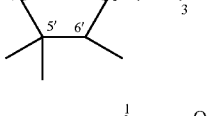

Formula VIII

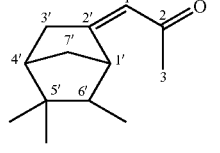

Formula IX

Those with the skill in the art will appreciate that

Formula II is 2-methyl-1-bicyclo[2.2.1]hept-2'-yl-propan-2-ol;

Formula III is 2-methyl-1-(5'-methyl-bicyclo[2.2.1]hept-2'-yl)-propan-2-ol;

Formula IV is 2-methyl-1-(6'-methyl-bicyclo[2.2.1]hept-2'-yl)-propan-2-ol;

Formula V is 1-(5',6'-dimethyl-bicyclo[2.2.1]hept-2-yl)-2'-methyl-propan-2-ol;
Formula VI is 1-(5',5'-dimethyl-bicyclo[2.2.1]hept-2-yl)-2'-methyl-propan-2-ol;
Formula VII is 2-methyl-1-(5',5',6'-trimethyl-bicyclo[2.2.1] hept-2'-yl)-propan-2-ol;
Formula VIII is 1-(5',5',6'-trimethyl-bicyclo[2.2.1]hept-2'-ylidene)-propan-2-one; and Formula IX is 1-(5',5',6'-trimethyl-bicyclo[2.2.1]hept-2'-yl)-propan-2-one.

The compounds of the present invention may be prepared with cyclopent-3-enyl-acetaldehydes via a Knoevenagel reaction followed by a cyclization reaction. Those with the skill in the art will appreciate that suitable cyclopent-3-enyl-acetaldehydes include, for example, (cyclopent-3'-enyl)-acetaldehyde, (3'-methyl-cyclopent-3'-enyl)-acetaldehyde, (2'-methyl-cyclopent-3'-enyl)-acetaldehyde, (2',3'-dimethyl-cyclopent-3'-enyl)-acetaldehyde, (2',2'-dimethyl-cyclopent-3'-enyl)-acetaldehyde, and (2',2',3'-trimethyl-cyclopent-3'-enyl)-acetaldehyde.

The reaction steps can be depicted by a general scheme as follows, wherein the broken lines indicate one double bond located between the carbon atom at position 3 and the carbon atom at position 2 or 4:

In these preparations, the compounds of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle,

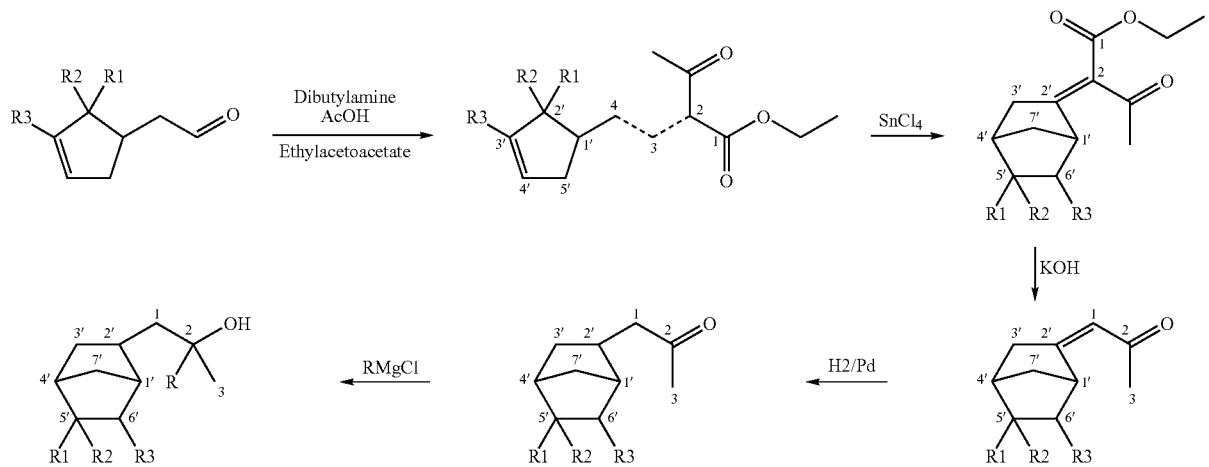

Those with skill in the art will recognize that some of the compounds of the present invention have a number of chiral centers, thereby providing numerous isomers of the claimed compounds. It is intended herein that the compounds described herein include isomeric mixtures of such compounds, as well as those isomers that may be separated using techniques known to those having skill in the art. Suitable techniques include chromatography such as high performance liquid chromatography, referred to as HPLC, and particularly gel chromatography and solid phase microextraction, referred to as SPME.

The use of the compounds of the present invention is widely applicable in current perfumery products, including the preparation of perfumes and colognes, the perfuming of personal care products such as soaps, shower gels, and hair care products, fabric care products as well as air fresheners and cosmetic preparations. The present invention can also be used to perfume cleaning agents, such as, but not limited to detergents, dishwashing materials, scrubbing compositions, window cleaners and the like.

hyacinth, jasmine, lilac, lily, magnolia, mimosa, narcissus, freshly-cut hay, orange blossom, orchid, reseda, sweet pea, trefle, tuberose, vanilla, violet, wallflower, and the like.

Olfactory effective amount is understood to mean the amount of compound in perfume compositions the individual component will contribute to its particular olfactory characteristics, but the olfactory effect of the perfume composition will be the sum of the effects of each of the perfumes or fragrance ingredients. Thus the compounds of the invention can be used to alter the aroma characteristics of the perfume composition, or by modifying the olfactory reaction contributed by another ingredient in the composition. The amount will vary depending on many factors including other ingredients, their relative amounts and the effect that is desired.

The level of compounds of the invention employed in the perfumed article varies from about 0.005 to about 10 weight percent, preferably from about 0.5 to about 8 and most preferably from about 1 to about 7 weight percent. In addition to the compounds other agents can be used in conjunction with the fragrance. Well known materials such as surfactants, emulsifiers, polymers to encapsulate the fragrance can also be employed without departing from the scope of the present invention.

Another method of reporting the level of the compounds of the invention in the perfumed composition, i.e., the compounds as a weight percentage of the materials added to impart the desired fragrance. The compounds of the invention can range widely from 0.005 to about 70 weight percent of the perfumed composition, preferably from about 0.1 to about 50 and most preferably from about 0.2 to about 25 weight percent. Those with skill in the art will be able to employ the desired level of the compounds of the invention to provide the desired fragrance and intensity.

When used in a fragrance formulation this ingredient provides freshness making the fragrance top notes more desirable and noticeable. It also has a spicy peppery odor which is very commonly used in men's fragrances added for fragrance appropriateness and desirability. The woody part of it is very useful in both men's and women's fragrances adding body and substantivity to the finished product. All of these odor qualities found in this material assist in beautifying and enhancing the finished accord improving the performance of the other materials in the fragrance. The floral of it will beautify as well and makes the fragrance more desirable and add the perception of value. There is also the fruity side of it which is found in many fragrances today which happens to be very trendy, especially for the younger consumer.

The following are provided as specific embodiments of the present invention. Other modifications of this invention will be readily apparent to those skilled in the art. Such modifications are understood to be within the scope of this invention.

As used herein all percentages are weight percent unless otherwise noted, ppm is understood to stand for parts per million, L is understood to be liter, mL is understood to be milliliter, N is understood to be normality, Kg is understood to be kilogram, g is understood to be gram, and mmHg be millimeters (mm) of mercury (Hg). IFF as used in the examples is understood to mean International Flavors & Fragrances Inc., New York, N.Y., USA.

EXAMPLE I

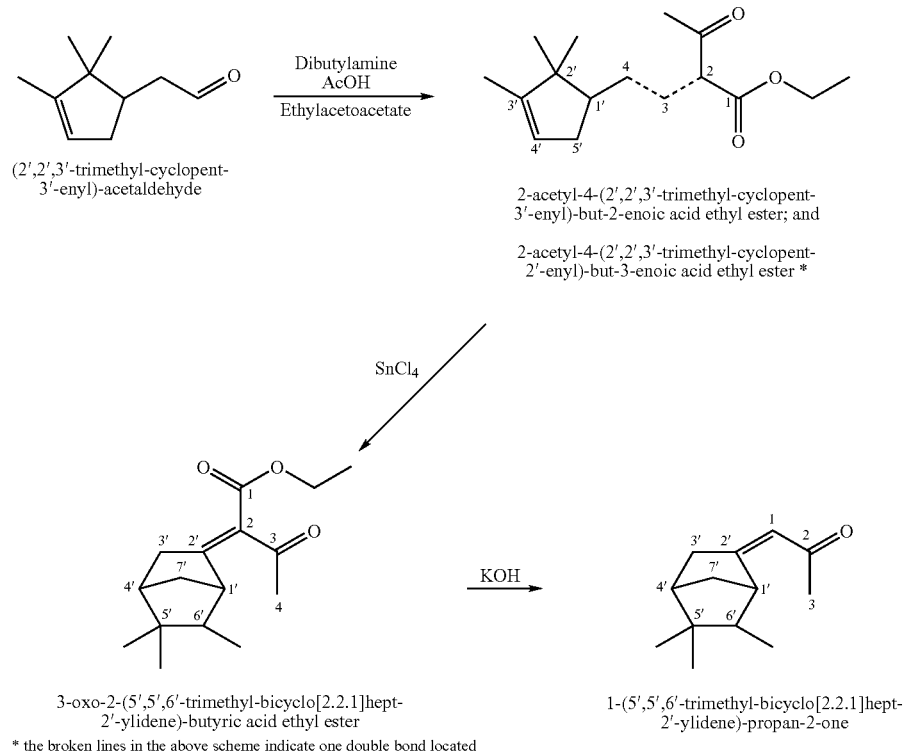

* the broken lines in the above scheme indicate one double bond located between the carbon atom at position 3 and the carbon atom at position 2 or 4.

Preparation of 1-(5',5',6'-trimethyl-bicyclo[2.2.1]hept-2'-ylidene)-propan-2-one: Ethyl acetoacetate (EAA) (1133 g, commercially available from Sigma-Aldrich Corp., St. Louis, Mo.) was added dropwise to a well stirred mixture of (2',2',3'-trimethyl-cyclopent-3'-enyl)-acetaldehyde (1204 g, commercially available from Atofina Chemicals NA, Inc., Philadelphia, Pa.), dibutylamine (91 g, commercially available from Sigma-Aldrich Corp., St. Louis, Mo.), and acetic acid (AcOH) (43 g, commercially available from Sigma-Aldrich Corp., St. Louis, Mo.) in 1 L toluene. The reaction temperature was maintained at about 12-15° C. with an ice-water bath. The reaction mixture was further stirred for overnight at room temperature, and gas chromatographic (GC) analysis indicated the reaction was completed. The reaction mixture was then poured into 1 N aqueous HCl (1 L) and the organic phase was separated and washed with 50% brine, saturated aqueous sodium bicarbonate, and water. The low boiling components, including the solvent of toluene, were removed under a reduced pressure to furnish the mixture of 2-acetyl-4-(2',2',3'-trimethyl-cyclopent-3'-enyl)-but-2-enoic acid ethyl ester and 2-acetyl-4-(2',2',3'-trimethyl-cyclopent-3'-enyl)-but-3-enoic acid ethyl ester (1913 g). Tin chloride (SnCl$_4$) (40 mL) was then added. The reaction mixture was stirred for overnight at 80° C. till GC analysis indicated the reaction was completed. The reaction mixture was then poured into 5% aqueous HCl (1 L). The organic phase was separated and washed with 50% brine and water, to provide 3-oxo-2-(5',5',6'-trimethyl-bicyclo[2.2.1]hept-2'-ylidene)-butyric acid ethyl ester. Water (900 mL) followed by potassium hydroxide (KOH) (840 g) were then added in small portions. The mixture was heated at 88° C. for two hours till GC analysis indicated the reaction was completed. The reaction mixture was poured into 3 N aqueous HCl (1.5 L). The organic phase was separated and washed with 50% brine and water, respectively. The crude product was distilled under a reduced pressure to produce 1-(5',5',6'-trimethyl-bicyclo[2.2.1]hept-2'-ylidene)-propan-2-one (695 g).

Mixture of 2-acetyl-4-(2',2',3'-trimethyl-cyclopent-3'-enyl)-but-2-enoic acid ethyl ester and 2-acetyl-4-(2',2',3'-trimethyl-cyclopent-3'-enyl)-but-3-enoic acid ethyl ester $^1$H NMR: 0.72-1.07 ppm (m), 1.23-1.36 ppm (m), 1.65-1.97 ppm (m), 2.12-2.49 ppm (m), 4.08-4.43 ppm (m), 5.23 ppm (s), 5.65-5.97 ppm (m), 6.90 ppm (t, J=7.8 Hz), 6.97 ppm (t, J=7.8 Hz)

3-Oxo-2-(5',5',6'-trimethyl-bicyclo[2.2.1]hept-2'-ylidene)-butyric acid ethyl ester $^1$H NMR: 0.90-1.08 ppm (m, 9H), 1.24-1.43 ppm (m, 5H), 1.86-1.94 ppm (m, 2H), 2.21-2.33 ppm (m, 3H), 2.34-2.45 ppm (m, 1H), 2.74 ppm (s, 1H), 2.79-2.86 ppm (m, 1H), 4.16-4.32 ppm (m, 2H)

1-(5',5',6'-Trimethyl-bicyclo[2.2.1]hept-2'-ylidene)-propan-2-one $^1$H NMR: 0.91-0.94 ppm (m, ~90% of 9H), 0.96-1.00 ppm (m, ~10% of 9H), 1.20-1.33 ppm (m, 2H), 1.82-1.90 ppm (m, 2H), 2.16 ppm (s, 3H), 2.26-2.45 ppm (m, 2H), 2.94-3.00 ppm (m, ~79% of 1H), 3.48 ppm (s, ~21% of 1H), 5.98 ppm (s, ~24% of 1H), 6.18 ppm (s, ~76% of 1H)

The product compound 1-(5',5',6'-trimethyl-bicyclo[2.2.1]hept-2'-ylidene)-propan-2-one was described as having woody, fruity, fresh, resin, and apple notes.

EXAMPLE II

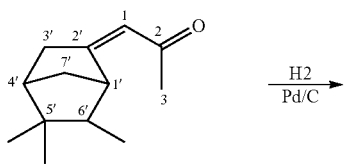

1-(5',5',6'-trimethyl-bicyclo[2.2.1]hept-2'-ylidene)-propan-2-one

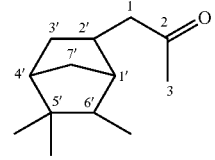

1-(5',5',6'-trimethyl-bicyclo[2.2.1]hept-2'-yl)-propan-2-one

Preparation of 1-(5',5',6'-trimethyl-bicyclo[2.2.1]hept-2'-yl)-propan-2-one: In an autoclave, 1-(5',5',6'-trimethyl-bicyclo[2.2.1]hept-2'-ylidene)-propan-2-one (490 g), 5% palladium (Pd) on carbon (3.6 g), and 2-propanol (100 g) were mixed and stirred at about 70-100° C. for two hours till GC analysis indicated the reaction was completed. The reaction mixture was filtered and distilled under a reduced pressure to produce 1-(5',5',6'-trimethyl-bicyclo[2.2.1]hept-2'-yl)-propan-2-one (400 g).

$^1$H NMR: 0.82 ppm (d, 3H, J=7.30 Hz), 0.87 ppm (s, 3H), 0.96 ppm (s, 3H), 1.18-1.20 ppm (m, 2H), 1.41-1.47 ppm (m, 1H), 1.62-1.69 ppm (m, 3H), 1.82-1.84 ppm (m, 1H), 2.14 ppm (s, 3H), 2.19-2.28 ppm (m, 1H), 2.49-2.59 ppm (m, 2H)

The product compound was described as having woody, ionone, and powdery notes.

EXAMPLE III

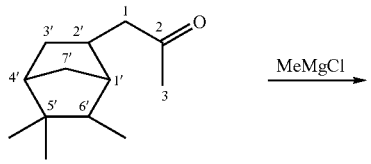

1-(5',5',6'-trimethyl-bicyclo[2.2.1]hept-2'-yl)-propan-2-one

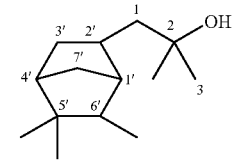

2-methyl-1-(5',5',6'-trimethyl-bicyclo[2.2.1]hept-2'-yl)-propan-2-ol

Preparation of 2-methyl-1-(5',5',6'-trimethyl-bicyclo[2.2.1]hept-2'-yl)-propan-2-ol: A solution of 1-(5',5',6'-trimethyl-bicyclo[2.2.1]hept-2'-yl)-propan-2-one (270 g) in 500 mL toluene was added dropwise to a mixture of 3 N methylmagnesium chloride (733 mL) and 500 mL toluene at 5° C. Upon completion of adding, GC analysis indicated that the reaction was complete. The reaction mixture was quenched carefully with 50% aqueous NaOH (200 g), and refluxed for 20 minutes. The liquid was decanted from the mixture and the organic phase was separated and washed with 50% brine and water. The crude product was distilled under a reduced pressure to produce 2-methyl-1-(5',5',6'-trimethyl-bicyclo[2.2.1]hept-2'-yl)-propan-2-ol (172 g).

$^1$H NMR: 0.82 ppm (d, 3H, J=7.29 Hz), 0.87 ppm (s, 3H), 0.97 ppm (s, 3H), 1.14-1.19 ppm (m, 1H), 1.21 ppm (s, 3H), 1.23 ppm (s, 3H), 1.24-1.28 ppm (m, 1H), 1.33-1.38 ppm (m, 1H), 1.43-1.63 ppm (m, 4H), 1.65-1.69 ppm (m, 2H), 1.80-1.83 ppm (m, 1H), 1.88-1.93 ppm (m, 1H)

The compound was described as having woody, mossy, tree bark, and patchouli notes.

EXAMPLE IV

The fragrance formula exemplified as follows demonstrates that the propanol compound imparts a woody character to the fragrance formula:

| Ingredients | Parts* + | Parts* − |
|---|---|---|
| AMYL SAL | 1.00 | 1.00 |
| BERGAMOT OIL ITALY MPF"PFG" BLO BHT | 10.00 | 10.00 |
| CLOVE BUD OIL USP | 0.20 | 0.20 |
| COUMARIN | 1.00 | 1.00 |
| CYCLACET | 3.00 | 3.00 |
| DIHYDRO MYRCENOL | 2.00 | 2.00 |
| DIPROPYLENE GLYCOL | 6.40 | 9.40 |
| 2-METHYL-1-(5',5',6'-TRIMETHYL-BICYCLO[2.2.1]HEPT-2'-YL)-PROPAN-2-OL | 3.00 | — |
| GALAXOLIDE 50 PCT BB | 20.00 | 20.00 |
| HEDIONE BHT | 5.00 | 5.00 |
| HEXENOL,B,GAMMA EXTRA 10% DPG | 2.00 | 2.00 |
| IONONE BETA EXTRA | 0.50 | 0.50 |
| ISO BUTYL QUINOLINE RD"PFG" | 1.00 | 1.00 |
| ISO E SUPER BHT | 20.00 | 20.00 |
| LINALYL ACET | 1.00 | 1.00 |
| LYRAL BHT | 7.00 | 7.00 |
| MANDARIN OIL HP"PFG" | 7.00 | 7.00 |
| NUTMEG OIL EI"PFG" | 1.00 | 1.00 |
| ORANGE OIL FLA TYPE CP"FLG" | 2.50 | 2.50 |
| TRISAMBER (ELINCS) 10% DPG | 1.00 | 1.00 |
| UNDECAVERTOL MVB | 1.00 | 1.00 |
| VERAMOSS | 0.40 | 0.40 |
| VERTOFIX COEUR | 4.00 | 4.00 |
| TOTAL | 100.00 | 100.00 |

*"+" represents a propanol compound containing formula; and "−" represents a propanol compound non-containing formula.

What is claimed is:

1. A method of improving, enhancing or modifying a fragrance formulation through the addition of an olfactory acceptable amount of a compound of formula:

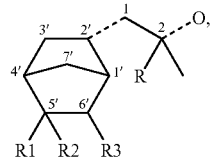

wherein R is absent, hydrogen or methyl;
R1, R2, and R3 are independently hydrogen or methyl; and
the broken lines represent independently single or double bonds, with the proviso that when R1, R2, and R3 are hydrogen, R is methyl.

2. The method of claim 1, wherein the compound is 2-methyl-1-(5',5',6' trimethyl-bicyclo[2.2.1]hept-2'-yl)-propan-2-ol.

3. The method of claim 1, wherein the compound is 1-(5',5',6'-trimethyl bicyclo[2.2.1]hept-2'-ylidene)-propan-2-one.

4. The method of claim 1, wherein the compound is 1-(5',5',6'-trimethyl-bicyclo [2.2.1]hept-2'-yl)-propan-2-one.

5. The method of claim 1, wherein the fragrance formulation is incorporated into a product selected from the group consisting of a perfume, a cologne, a toilet water, a cosmetic product, a personal care product, a fabric care product, a cleaning product, and an air freshener.

6. The method of claim 1, wherein the cleaning product is selected from the group consisting of a detergent, a dishwashing composition, a scrubbing compound, and a window cleaner.

7. The method of claim 1, wherein the olfactory acceptable amount is from about 0.005 to about 10 weight percent of the fragrance formulation.

8. The method of claim 1, wherein the olfactory acceptable amount is from about 0.5 to about 8 weight percent of the fragrance formulation.

9. The method of claim 1, wherein the olfactory acceptable amount is from about 1 to about 7 weight percent of the fragrance formulation.

10. A compound 2-methyl-1-(5',5',6'-trimethyl-bicyclo [2.2.1]hept-2'-yl)-propan-2-ol.

11. A fragrance formulation containing the compound of claim 10.

12. A fragrance product containing the compound of claim 10.

* * * * *